United States Patent
Gerner

(10) Patent No.: US 8,202,321 B2
(45) Date of Patent: Jun. 19, 2012

(54) IMPLANT

(75) Inventor: Leonie Gerner, Ulm (DE)

(73) Assignee: ULRICH GmbH & Co. KG, Ulm (DE)

( * ) Notice: Subject to any disclaimer, the term of this patent is extended or adjusted under 35 U.S.C. 154(b) by 359 days.

(21) Appl. No.: 12/485,986

(22) Filed: Jun. 17, 2009

(65) Prior Publication Data

US 2010/0324686 A1 Dec. 23, 2010

(51) Int. Cl.
*A61F 2/44* (2006.01)
(52) U.S. Cl. ............ 623/17.15; 623/17.11; 623/17.16
(58) Field of Classification Search .... 623/17.11–17.16; 403/164, 165, 190, 289
See application file for complete search history.

(56) References Cited

U.S. PATENT DOCUMENTS

| | | | | |
|---|---|---|---|---|
| 5,776,197 | A * | 7/1998 | Rabbe et al. | 623/17.15 |
| 6,344,057 | B1 * | 2/2002 | Rabbe et al. | 623/17.11 |
| 6,808,538 | B2 | 10/2004 | Paponneau | 623/17.16 |
| 7,048,739 | B2 * | 5/2006 | Konieczynski et al. | 606/288 |
| 7,060,099 | B2 * | 6/2006 | Carli et al. | 623/17.14 |
| 7,575,599 | B2 * | 8/2009 | Villiers et al. | 623/17.14 |
| 7,575,601 | B2 | 8/2009 | Dickson | |
| 2005/0004572 | A1 | 1/2005 | Biedermann et al. | |
| 2005/0187632 | A1 * | 8/2005 | Zubok et al. | 623/17.14 |
| 2007/0028710 | A1 | 2/2007 | Kraus et al. | |

FOREIGN PATENT DOCUMENTS

| | | |
|---|---|---|
| DE | 4109941 A1 | 10/1992 |
| WO | 2004103225 A1 | 12/2004 |

* cited by examiner

*Primary Examiner* — Kevin T Truong
*Assistant Examiner* — Christian Sevilla
(74) *Attorney, Agent, or Firm* — Andrew Wilford

(57) ABSTRACT

An implant for use between two axially separated vertebrae has a body extending axially between the vertebrae and having longitudinally outwardly directed ends juxtaposed with the vertebrae and each formed with a radially outwardly projecting annular rounded ridge and with a radially outwardly open groove axially inward of the ridge. A respective end plate at each of ends bears axially outwardly directly on the respective vertebra and is formed with a radially inwardly open rotation-symmetrical recess receiving the respective end of the body. This recess is formed with an annular inwardly open groove having an inner surface on which rides the respective ridge with freedom for swiveling of each end plate on the respective end.

7 Claims, 2 Drawing Sheets

IMPLANT

FIELD OF THE INVENTION

The invention concerns an implant for insertion between the vertebrae of the spinal column with a body that has an end plate on at least one of its free ends.

BACKGROUND OF THE INVENTION

Implants of this type are used, for example, to be able to reestablish stability in cases of degenerative or traumatic diseases of the spinal column, the body being used, for example, as a longitudinal place holder to bridge the distance between neighboring vertebrae because of the complete or partial ablation of a diseased vertebra. In practice, an implants of this type is also used as a replacement for a removed spinal disk. The end plate serves to reduce the surface pressure. It was found to be disadvantageous in implants of this type that with such implants no adjustment to the natural curvature of the spinal column is possible, so that in the prior art it was further proposed to provide a hinge-like connection between the body and the end plate so the end plate can be pivoted around an axis of rotation relative to the body. Concerning this, reference can be made, for example, to U.S. Pat. No. 6,808,538 that shows an implant with a body having at its ends pins that are opposite to each other, starting from which the lateral edges of the implant drop off at an angle. The end plate can be clipped onto these pins and shifted in the area of the angle that is specified by the slope of the sides.

OBJECT OF THE INVENTION

The object of the invention is to solve the problem of designing the implant described above in such a way that an improved adjustability to the individual situation of the patient is possible.

SUMMARY OF THE INVENTION

This object is attained in the implant described above in that in the end plate on the side turned toward the body, a rotation-symmetric recess is formed that is guided by its wall surface on an annular ridge that is bounded by an annular groove of the body.

This embodiment has the advantage that a polyaxial joint is made available in which the possibility of deviation is not limited to the axis of deviation, but, dependent on the specific implantation site, as well as on the individual curvature of the spinal column of the patient, rotation of the end plate relative to the body can take place as a result of the symmetry of rotation of the recess around different axis of rotation, so that an automatic adjustment of the angle between the end plate and the body takes place in the sagittal and frontal profile during implantation. It must also be noted that the symmetry of rotation of the recess also makes it possible that a twisting about the longitudinal axis of the body of the end plate takes place, as construction components are not used that hinder such rotation, as still takes place as a result of the pins in U.S. Pat. No. 6,808,538.

Additional advantages of the implant according to the invention are that the implant system that is to be made available to the surgeon can consist of fewer components, as several angles can be covered with a (preassembled) implant, so that as a result of the simpler implant system storage costs for hospitals as well as for manufacturers are reduced.

It is to be noted further that in the implant according to the invention, the placement of the end plates on the body essentially takes place on the sides, as the end plate with the recess engages laterally around the annular ridge, so that the annular groove serves to make the swiveling of the end plate on the body possible.

In this connection it is preferred when the wall surface is concavely curved in horizontal cross section and the annular ridge has a rounded outer surface in the longitudinal direction of the body so that continuous displacement of the end plate is possible with respect to the body.

Once again preferred in this connection is that the surfaces of the recess that are designated to abut one another as well as the annular ridge correspond to sections of a hollow sphere or sphere, as the characteristics of a spherical joint with a spherical head and a spherical bearing cup are recreated and with a correspondingly wide embrace of the annular ridge by the wall surface of the recess, accurate positioning of the annular ridge in the recess can be achieved.

However, when a correspondingly wide embrace is dispensed with or when the annular ridge is to be provided only with limited thickness compared to the depth of the recess, in order to generate an additional degree of freedom of movement, it is advisable that the recess on the side turned toward the body be provided with a ridge that narrows the width of the opening for engagement with the annular groove, which ensures good anchoring.

It is further advantageous when the width of the annular groove essentially correspond to the depth of the recess as this way the wall surfaces of the annular grove do not limit the possibility of pivoting of the end plate with respect to the body.

An especially preferred embodiment within the framework of the invention is characterized in that the body is a sleeve and the end plate is provided with a through hole that communicates with the passage of the sleeve, which can especially also end at the recess. With this design, a large open interior space is made available that can be filled with autologous or homologous bone material or other fill materials so that in this way growing in of the implant is promoted. This goal is also assisted by holes in the wall of the sleeve.

In order to simplify connection of the end plate with the body for assembling the implant there is the possibility that the end plate be provided with a slot reaching from the outer surface to the through hole and the thereby formed arms of the circular end plate can be detachably connected, for example by a screw connection.

An alternative possibility of the connection is that the ridge and perhaps the surface of the annular ridge are formed with screwthreads, so that the ridge can be screwed over the annular ridge in such a way that the ridge enters into the annular grove and free rotatability of the polyaxial joint is achieved.

BRIEF DESCRIPTION OF THE DRAWING

In the following, the invention is described in detail with reference to embodiments shown in the drawing; therein.

DETAILED DESCRIPTION

Figure 1:
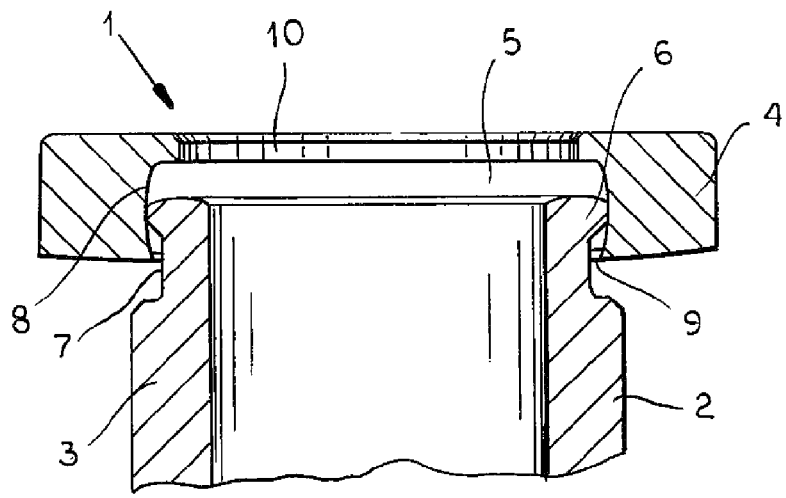
FIG. 1 is a longitudinal section through an implant in accordance with the invention at an angle of 0° degrees to the end plate of the implant.
Figure 2:
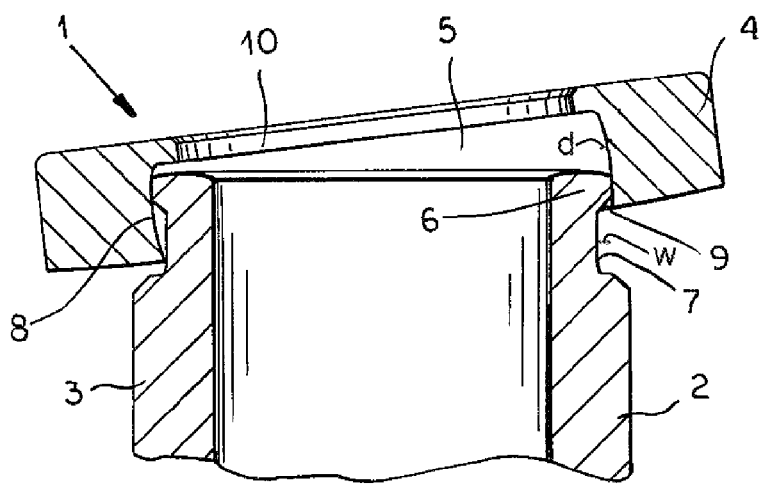
FIG. 2 is a view like FIG. 1 with the end plate canted somewhat to the implant.
Figure 3:
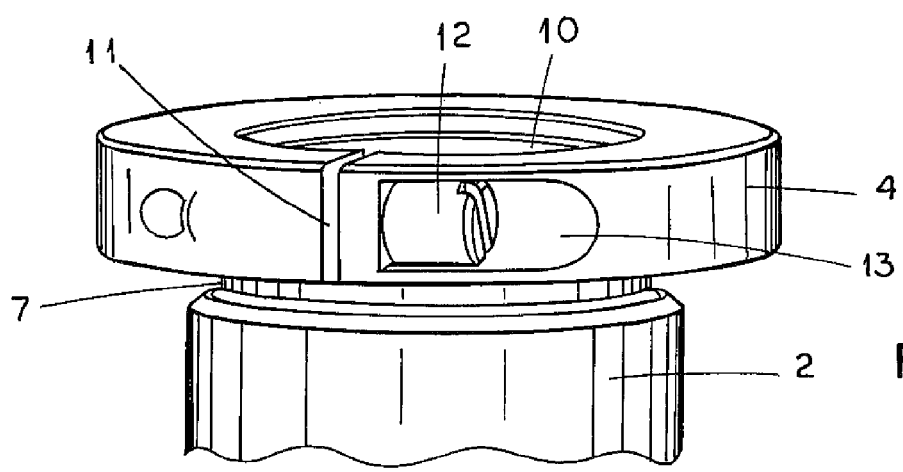
FIG. 3 is a perspective view of an implant with an end plate having a throughgoing hole and a screw connection.

In the drawing in FIGS. 1 to 3, two embodiments of an implant 1 are shown for insertion between vertebrae of the spinal column as replacement of partially or completely removed vertebrae. This implant 1 has a body 2 formed as a sleeve 3 whose wall is formed with holes 14. On at least one of the free ends of the body 2, but preferably at both free ends, an end plate 4 is mounted that has a rotation-symmetric recess 5 on the side turned toward the body 2. The end of the body 2 is formed with an annular ridge 6 that is bounded inwardly by an annular groove 7, this annular ridge 6 serving to guide the end plate over a wall surface 8 of the recess 5. To this end, the surface 8 is curved concavely in horizontal cross section and the annular ridge 6 has a rounded outer surface, whereby in the embodiment shown the surface of the recess 5 as well as of the annular ridge 6 correspond to sections of a hollow or solid sphere.

In the embodiment shown in the drawing, the recess 5 also is formed on its edge turned toward the body 2 with a ridge 9 that narrows the width of the recess mouth for engagement with the annular groove 7, which can also be designed as screwthread in order to make interaction with a corresponding thread of the annular ridge 6, a screwing in of the end plate into the body 2 possible until after exiting of the thread on the side of the end plate into the groove 7, the degrees of freedom of movement of the end plate with respect to the body 2 being given again, namely for one, the rotatability about a longitudinal axis of the body 2, as well as a polyaxial deviation depending on the specific marginal conditions that occur during implantation.

FIGS. 1 and 2 show that a width w of the groove 7 essentially corresponds to a depth d of the recess 5.

FIG. 3 shows an embodiment in which the end plate is provided with a slot 11 that extends from the outer surface inward to a central hole 10, and the thereby formed arms of the circular the end plate that are detachably connected with each other via a screw 12 that engages with a thread in one of the these arms. The head of the screw is sunk into a counterbore 13 in the other of these arms.

Figure 4:
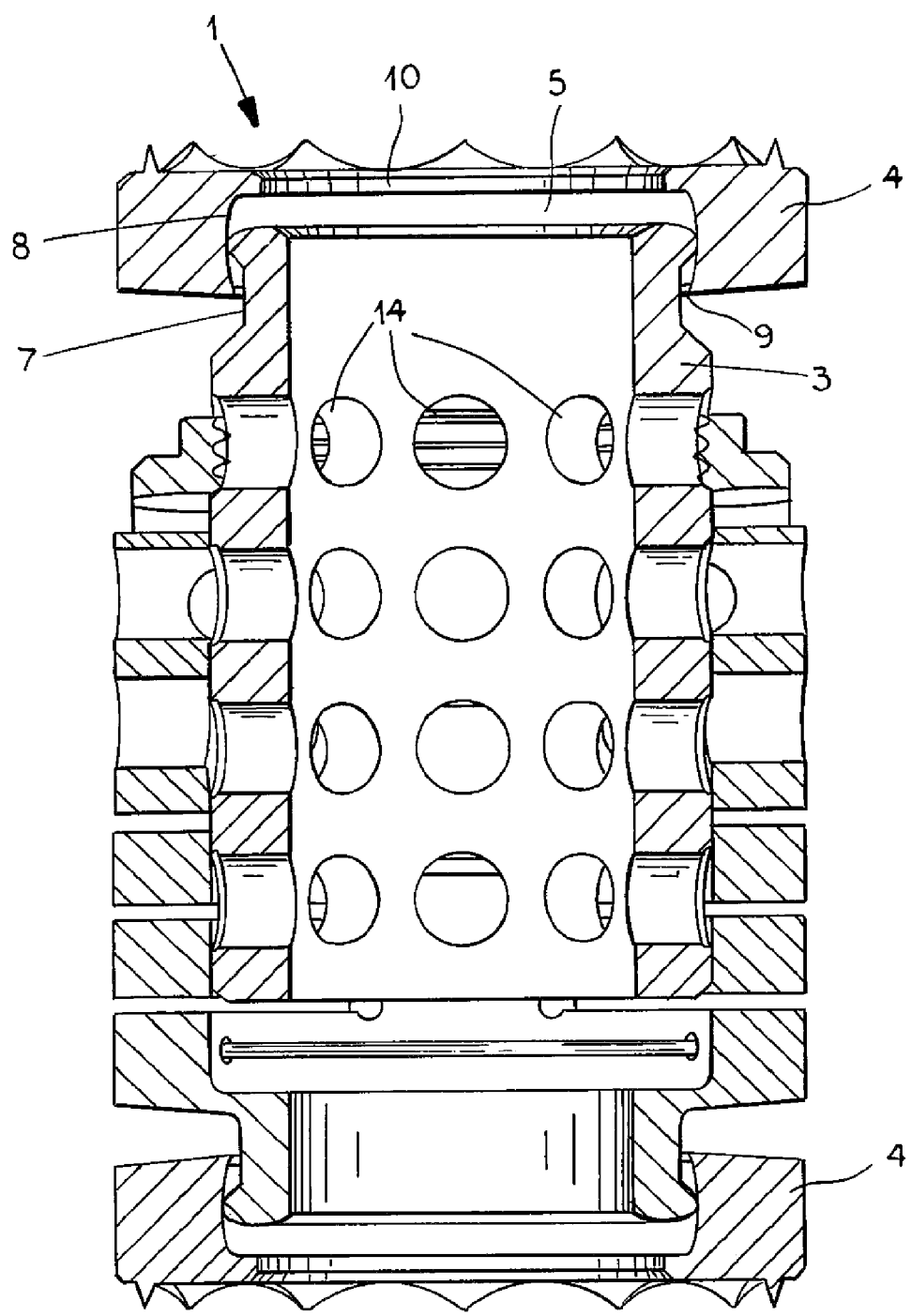
FIG. 4 is a longitudinal section of an implant with two end plates.

FIG. 4 shows a complete implant 1 with two end plates 4 at opposite ends from one another that can each assume a respective angular position on the respective vertebra. The sleeve body 3 has several openings in its circumference that make filling and/or improved growing in of the implant 1 possible.

The invention claimed is:

1. An implant for insertion between two axially separated vertebrae as replacement for a missing vertebra, the implant comprising:
   a tubular body having two axially separated and longitudinally outwardly directed ends juxtaposable with respective vertebrae, each of the ends being formed with a radially outwardly projecting annular rounded ridge and with a radially outwardly open groove axially inward of the respective ridge, the ridges each having a rotation-symmetrical and radially outwardly convex outer surface;
   a respective end plate extending axially outward from each of the ends and formed with
   a central hole that communicates with an interior of the body,
   a radially throughgoing slot extending to the central hole and thereby forming the ring into a pair of arms, and
   a radially inwardly open recess receiving the annular ridge of the respective end of the body and having an annular rotational-symmetrical and radially inwardly concave inner surface on which rides the outer surface of the ridge of the respective end with freedom for polyaxial swiveling of each end plate on the respective end; and
   respective screws in the plates each having a threaded shank threaded into one of the respective arms and a head bearing on the other of the respective arms for pulling the respective arms together and thereby tightening the respective end plate on the respective ridge.

2. The implant according to claim 1 wherein the inner surfaces are concavely curved in horizontal cross section and the outer surface is rounded in a longitudinal direction of the body.

3. The implant according to claim 2 wherein the inner surfaces of the recesses as well as the outer surfaces of the annular ridges correspond to sections of a surface of a sphere.

4. The implant according to claim 2 wherein the recesses each have on a side turned toward the body a ridge that narrows the opening for engagement with the respective annular groove.

5. The implant according to claim 1 wherein widths of the annular grooves correspond essentially to depths of the respective recesses.

6. The implant defined in claim 1 wherein both the inner surfaces and the outer surfaces are part-circular in section.

7. The implant defined in claim 1 wherein the grooves each have an axial length generally equal to a width measured axially of the inner surface of the end-plate groove.

* * * * *